United States Patent
Kim et al.

(10) Patent No.: US 7,829,698 B2
(45) Date of Patent: Nov. 9, 2010

(54) NANO-PARTICLES COMPRISING CUCURBITURIL DERIVATIVES, PHARMACEUTICAL COMPOSITION CONTAINING THE SAME, AND PROCESS FOR THE PREPARATION THEREOF

(75) Inventors: Kimoon Kim, Pohang (KR); Sang Yong Jon, Pohang (KR); Young Jin Jeon, Pohang (KR); Dong Hyun Oh, Pohang (KR); Narayanan Selvapalam, Pohang (KR)

(73) Assignee: Postech Foundation, Pohang (KR)

( * ) Notice: Subject to any disclaimer, the term of this patent is extended or adjusted under 35 U.S.C. 154(b) by 0 days.

(21) Appl. No.: 12/175,980

(22) Filed: Jul. 18, 2008

(65) Prior Publication Data

US 2008/0279950 A1   Nov. 13, 2008

Related U.S. Application Data

(62) Division of application No. 10/565,834, filed as application No. PCT/KR2004/001874 on Jul. 26, 2004, now abandoned.

(30) Foreign Application Priority Data

Jul. 26, 2003   (KR)   .................. 1020030051841

(51) Int. Cl.
   *C07D 487/04*   (2006.01)
(52) U.S. Cl. .............. 540/460; 514/183; 514/387; 514/388
(58) Field of Classification Search .......... 514/44, 514/58, 183, 387, 388; 435/4, 174
   See application file for complete search history.

(56) References Cited

U.S. PATENT DOCUMENTS

| 6,365,734 B1 * | 4/2002 | Kim et al. .............. 540/460 |
| 7,550,441 B2 * | 6/2009 | Farokhzad et al. ........ 514/44 R |
| 2002/0133003 A1 | 9/2002 | Kim et al. |
| 2003/0008818 A1 * | 1/2003 | Pun et al. .............. 514/12 |
| 2003/0017972 A1 * | 1/2003 | Pun et al. .............. 514/8 |
| 2004/0147396 A1 | 7/2004 | Richter et al. |

FOREIGN PATENT DOCUMENTS

| DE | 196 03 377 A1 | 8/1997 |
| JP | 2001-122877 | 5/2001 |
| KR | 1020040072810 A | 8/2004 |
| WO | 0068232 A1 | 11/2000 |
| WO | WO 00/68232 A1 | 11/2000 |
| WO | 02/080910 | 10/2002 |
| WO | 02096553 A2 | 12/2002 |
| WO | WO 02/096553 A2 | 12/2002 |
| WO | 03004500 A1 | 1/2003 |
| WO | WO 03/004500 A1 | 1/2003 |
| WO | 03024978 A1 | 3/2003 |
| WO | WO 03/024978 A1 | 3/2003 |
| WO | 03055888 A1 | 7/2003 |
| WO | WO 03/055888 A1 | 7/2003 |
| WO | WO 03055888 | * 7/2003 |

OTHER PUBLICATIONS

Supplementary European Search Report from EP appln. No. 04 77 4205, dated Jul. 7, 2009, 6 pages.
S. Jon et al.: "Facile Synthesis of Cucurbit[n]uril Derivatives via Direct Functionalization: Expanding Utilization of Cucurbit[n]uril," Journal of the American Chemical Society, vol. 125, No. 34, pp. 10186-10187, Jan. 1, 2003.
Samsonenko et al.: "Sythesis and crystal structure of the nanosized supramolecular SmIII complex with macrocyclic cavitand cucurbituril" Russian Chemical Bulletin, vol. 51, No. 10, pp. 1915-1918, 2000 (Abstract).
Supplementary European Search Report, EP appl. No. 04774205, Aug. 12, 2008, 4 pages.
S. Y. Jon, et al.: "Facile Sythesis of Cucurbit[n]uril Derivatives via Direct Functionalization: Expanding Utilization of Cucurbit[n]uril," J. Am. Chem. Soc., vol. 125, No. 34, pp. 10186-10187, 2003.
Freeman, W.A., et al., "Cucurbituril", J. Am. Chem. Soc., 103, 1981, pp. 7367-7368.
Kim, J., et al., "New Cucurbituril Homologues: Syntheses, Isolation, Characterization, and X-ray Crystal Structures . . . ", J. Am. Chem. Soc., 122, 2000, pp. 540-541.
Isobe, H., et al., "Ternary Complexes Between DNA, Polyamine, and Cucurbituril: A Modular Approach to DNA-Binding Molecules", Angew. Chem. Int. Ed., 39, 2000, pp. 4257-4260.
Lee, J.W., et al., "Novel Pseudorotaxane-Terminated Dendrimers: Supramolecular Modification of Dendrimer Periphery", Angew. Chem. Int. Ed., 40, No. 4, 2001, pp. 746-749.
Flinn, A., et al., "Decamethylcucurbit[5]uril", Angew. Chem. Int. Ed., 31, 1992, pp. 1475-1477.
Behrend, R. et al., "Ueber Condensationsproducte aus Glycoluril und Formaldehyd", Justus Liebig's Ann. Chem., 339, 1905, pp. 1-37.

* cited by examiner

*Primary Examiner*—Michael G Hartley
*Assistant Examiner*—Jagadishwar R Samala
(74) *Attorney, Agent, or Firm*—Rothwell, Figg, Ernst & Manbeck, pc

(57) ABSTRACT

Provided are nanoparticles prepared by the aggregation of cucurbituril derivatives and having a particle size of 1 to 1,000 nm, a pharmaceutical composition in which a pharmaceutically active substance is loaded into the nanoparticles, and preparation methods thereof.

7 Claims, 1 Drawing Sheet

NANO-PARTICLES COMPRISING CUCURBITURIL DERIVATIVES, PHARMACEUTICAL COMPOSITION CONTAINING THE SAME, AND PROCESS FOR THE PREPARATION THEREOF

CROSS REFERENCE TO RELATED APPLICATIONS

The present application is a divisional of U.S. patent application Ser. No. 10/565,834, filed on Jan. 25, 2006, which is a 35 USC §371 National Phase Entry Application from PCT/KR2004/001874, filed Jul. 26, 2004, and designating the United States. This application claims priority under 35 U.S.C. §119 based on Korean Patent Application No. 10-2003-0051841 filed Jul. 26, 2003, which are incorporated herein in their entireties.

BACKGROUND OF THE INVENTION

1. Field of the Invention

The present invention relates to nanoparticles including a cucurbituril derivative. More particularly, the present invention relates to nanoparticles prepared by the aggregation of cucurbituril derivatives, a pharmaceutical composition including the nanoparticles, and preparation methods thereof.

2. Description of the Related Art

As a considerable amount of genetic information is obtained by the completion of the human genome project in the 21$^{th}$ century, studies about diagnosis and prognosis of various diseases have been actively conducted. Under these circumstances, the development of new drugs and new drug delivery systems therefor has been a main target of numerous studies in the biotechnology industry. Even though the development of new drugs is a high value-added industry, high risk is imposed and enormous economical support is required. Furthermore, the development of new drugs is time-consuming because a complicated clinical test is necessary to achieve commercialization after development of new drugs. On the other hand, the development of new drug delivery systems requires reduced time and cost by about ⅓ of those required for the development of new drugs and has a very high success probability. The development of new drug delivery systems has been actively made by numerous domestic or foreign academic, industrial, and governmental research institutes. An example of newly developed and currently commercially available drug delivery systems in this country is a formulation of cyclosporin (trade name: Implanta) used as an immunosuppressant, exported from: Hanmi Pharmaceutical Co. (Korea) to Novartis. Another example is the development of Ketotop (Pacific Pharmaceutical Co., Korea). Based on the successful commercialization of developed drug delivery systems, extensive studies about drug delivery systems have been conducted by the departments of chemistry, chemical engineering, pharmacy, medicine, and the like of numerous domestic universities, the research institutes of pharmaceutical companies, governmental research institutes, and industrial chemistry-related research institutes. Furthermore, there have been done studies about various drug delivery systems for genes, proteins, and organic compounds, various administration methods such as oral, transdermal, and transnasal administration, and drug delivery systems targeted to specific organs such as the brain, the kidneys, and the liver. In foreign countries, research departments for drug delivery systems are organized at almost all major universities. Major foreign companies conducting studies about drug delivery systems include Alza Corp., Elan Corporation, plc., Dura Pharmaceuticals Inc., Andrx Corp., Vivus Inc., and the like.

Development of a drug delivery system requires a drug carrier and formulation. Synthesis of various polymers used as such a drug carrier has been predominantly studied. A representative of these synthetic polymers is a biodegradable polymer. In particular, a biodegradable polymer which is non-toxic in vivo, such as polylactide (PLA), poly(lactide-co-glycolide) (PLGA), polyethyleneglycol (PEG), and poly(alkylcyanoacrylate), has been actively studied for a drug delivery system.

The following important requirements in development of a drug delivery system must be satisfied: fewer side effects; formation of a stable formulation between a drug and a drug delivery system to prevent drug loss and degeneration and to ensure a stable drug delivery; and stable drug delivery to a targeted organ or cell.

Continuous development of various drug delivery systems satisfying the above requirements is required. Hitherto, however, there are not many drug delivery systems which are excellent in all of thermoplasticity, biocompatibility, biodegradability, productivity, processability, and the like. Therefore, development of promising new drug delivery systems is required. Furthermore, active participation in development of drug delivery systems which is an important technique for new drug development is required to keep pace with world-wide studies about development of various drug delivery systems.

Cucurbituril was first reported by R. Behrend, E. Meyer, F. Rusche in 1905 (*Liebigs Ann. Chem.* 1905, 339, 1). According to their report, the condensation of glycoluril and excess formaldehyde in the presence of hydrochloric acid (HCl) produces an amorphous solid. Dissolution of the amorphous solid in hot concentrated sulfuric acid and then dilution of the resultant solution with water produce a crystalline substance. However, they wrongly characterized this substance as $C_{10}H_{11}N_7O_4 \cdot 2H_2O$ without revealing the structure of this substance.

In 1981, this substance was rediscovered by W. Mock and coworkers. They correctly characterized it as a hexameric macrocyclic compound with the chemical formula of $C_{36}H_{36}N_{24}O_{12}$ which was confirmed by X-ray crystal structure determination (*J. Am. Chem. Soc.* 1981, 103, 7367). They named it cucurbit[6]uril. Since then, an improved synthetic method of cucurbit[6]uril has been disclosed (DE 196 03 377 A1).

In 2000, Kimoon Kim and coworkers reported the improved preparation and separation of the well-known cucurbit[6]uril and its homologues, cucurbit[n]urils (n=5, 7, 8), and identified their X-ray crystal structures (*J. Am. Chem. Soc.* 2000, 122, 540).

Meanwhile, WO 00/68232 discloses cucurbit[n]uril represented by Reference Diagram 1 below:

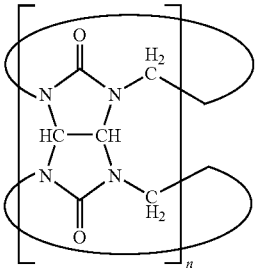

[Reference Diagram 1]

wherein n is an integer of 4 to 12.

The above-described cucurbituril derivatives are compounds including unsubstituted glycoluril monomer units.

Meanwhile, a cucurbituril derivative including substituted glycoluril monomer units was known (Angew, *Chem. Int. Ed. Engl.* 1992, 31, 1475). According to this document, decamethylcucurbit[5]uril including five dimethanodimethylglycoluril monomer units is synthesized by condensation between dimethylglycoluril and formaldehyde.

Cucurbituril is a macrocyclic compound and has a lipophilic cavity and two hydrophilic entrances at upper and lower portions. In this respect, lipophilic interactions occur in the cavity of cucurbituril, and hydrogen bonds, polar-polar interactions, and positive charge-polar interactions occur in the two entrances having six carbonyl groups. Therefore, cucurbituril has retention capacity for various compounds by very stable non-covalent bond with these compounds (see Table 1).

TABLE 1

Non-covalent coupling constant between cucurbituril and compounds

| Guest molecule | $K_f$ | Guest molecule | $K_f$ |
|---|---|---|---|
| $CH_3CH_2COOH$ | $5.9 \times 10^2 M^{-1}$ | Phe | $1.4 \times 10^3 M^{-1}$ |
| $NH_2(CH_2)_6NH_2$ | $2.7 \times 10^6 M^{-1}$ | L-Ala | $1.0 \times 10^3 M^{-1}$ |
| $Me(CH_2)_4NH_2$ | $2.4 \times 10^4 M^{-1}$ | L-Val | $1.4 \times 10^3 M^{-1}$ |
| $H_2N(CH_2)_5OH$ | $6.9 \times 10^2 M^{-1}$ | Phe-gly | $1.1 \times 10^3 M^{-1}$ |
| $H_2N(CH_2)_2COOH$ | $2.3 \times 10^3 M^{-1}$ | Leu-gly | $3.7 \times 10^2 M^{-1}$ |
| $H_2N(CH_2)_2CN$ | $4.4 \times 10^2 M^{-1}$ | Gly-val | $1.5 \times 10^3 M^{-1}$ |

As shown in Table 1, cucurbituril forms a complex, particularly, with a compound having an amino group or a carboxyl group by very stable non-covalent linkage. Based on such characteristics, studies about application of cucurbituril in various areas have been continuously conducted.

Recently, the present inventors reported a complex formation between oxaliplatin approved as an anticancer agent by the Food Drug Administration (FDA) and cucurbituril used as a drug delivery system by a stable non-covalent bond (PCT/KR02/01755). Furthermore, the present inventors reported an enhancement of DNA binding capacity by cucurbituril-containing pseudo-rotaxane and a use of a cucurbituril-based dendrimer as a gene delivery system [KR01-7169, Angew. Chem. Int. Ed., 2000 and 2001].

In addition, the present inventors found that a self-assembled monolayer made of cucurbituril, which is formed on a gold surface, has a reproducible and stable non-covalent binding capacity with proteins such as lysozyme and glucose oxidase (GOD).

In this regard, it is anticipated that cucurbituril cannot be used as a drug delivery system only for a single molecule drug having an amine group, an ammonium group, or a carboxyl group, but also for a protein or polypeptide drug. However, cucurbituril has a low solubility and no active functional groups that can be easily substituted by various substituents, and thus, its utility is extremely limited. For this reason, cucurbituril is subsidiary to cyclodextrin which is an existing promising drug delivery system. In spite of very excellent retention capacity of cucurbituril, extensive studies about a use of cucurbituril as a drug delivery system have not been conducted.

Recently, while searching for solutions to overcome the limitations in use of cucurbituril as a drug delivery system, the present inventors developed hydroxycucurbituril having twelve hydroxyl groups and diaminophenylcucurbituril having two aminophenyl groups as a result of introducing active substituted groups to cucurbiturils limitedly used [see Reference Diagram 2: Korean Patent Application No. 2003-0008453, PCT/KR02/02213].

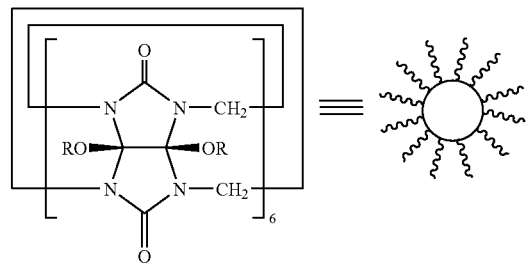

[Reference Diagram 2]

Various substituents can be easily introduced into the above-described hydroxycucurbituril, which enables synthesis of various cucurbituril derivatives.

Therefore, under the necessity of development of new drug delivery systems, the present invention was completed based on the above-described non-covalent binding properties of cucurbiturils and easy introduction of various substituents into cucurbituril derivatives.

SUMMARY OF THE INVENTION

The present invention provides nanoparticles including a cucurbituril derivative.

The present invention also provides a pharmaceutical composition in which a drug is loaded into the nanoparticles.

The present invention also provides a method of preparing the nanoparticles.

The present invention also provides a method of preparing the pharmaceutical composition.

DISCLOSURE OF THE INVENTION

According to an aspect of the present invention, there are provided nanoparticles prepared by the aggregation of cucurbituril derivatives of Formula 1 below and having a particle size of 1 to 1,000 nm:

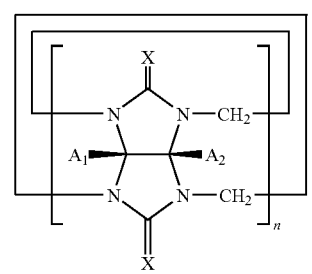

Formula 1 wherein X is O, S, or NH;
$A_1$ and $A_2$ are respectively $OR^1$ and $OR^2$, $SR^1$ and $SR^2$, or $NHR^1$ and $NHR^2$;
$R^1$ and $R^2$ are each independently selected from the group consisting of hydrogen, a substituted or unsubstituted alkyl of $C_1$-$C_{30}$, a substituted or unsubstituted alkenyl of $C_2$-$C_{30}$, a substituted or unsubstituted alkynyl of $C_2$-$C_{30}$, a substituted or unsubstituted carbonylalkyl of $C_2$-$C_{30}$, a substituted or unsubstituted thioalkyl of $C_1$-$C_{30}$, a substituted or unsubstituted alkylthiol of $C_1$-$C_{30}$, a substituted or unsubstituted alkoxy of $C_1$-$C_{30}$, a substituted or unsubstituted hydroxyalkyl of $C_1$-$C_{30}$, a substituted or unsubstituted alkylsilyl of $C_1$-$C_{30}$, a substituted or unsubstituted aminoalkyl of $C_1$-$C_{30}$, a substituted or unsubstituted aminoalkylthioalkyl of $C_1$-$C_{30}$, a substituted or unsubstituted cycloalkyl of $C_5$-$C_{30}$, a substituted or unsubstituted heterocycloalkyl of $C_2$-$C_{30}$, a substituted or unsubstituted aryl of $C_6$-$C_{30}$, a substituted or unsubstituted arylalkyl of $C_6$-$C_{20}$, a substituted or unsubstituted heteroaryl of $C_4$-$C_{30}$, and a substituted or unsubstituted heteroarylalkyl of $C_4$-$C_{20}$; and n is an integer of 4 to 20.

According to another aspect of the present invention, there is provided a pharmaceutical composition in which a pharmaceutically active substance is loaded as a guest molecule into nanoparticles formed by the aggregation of cucurbituril derivatives of formula 1 above.

According to another aspect of the present invention, there is provided a method of preparing nanoparticles by the agglomeration of cucurbituril derivatives, which includes: dissolving cucurbituril derivatives of Formula 1 in an organic solvent to obtain a reaction solution; adding water to the reaction solution followed by dispersing; distilling the dispersed solution in a temperature range from a boiling point of the organic solvent to 100° C. to remove the organic solvent; and cooling the resultant solution to room temperature.

According to yet another aspect of the present invention, there is provided a method of preparing a pharmaceutical composition in which a pharmaceutically active substance as a guest molecule is loaded into the above-prepared nanoparticles, which includes: dissolving a cucurbituril derivative of Formula 1 and the pharmaceutically active substance in an organic solvent to obtain a reaction solution; adding water to the reaction solution followed by dispersing; distilling the dispersed solution in a temperature range from a boiling point of the organic solvent to 100° C. to remove the organic solvent; and cooling the resultant solution to room temperature.

BRIEF DESCRIPTION OF THE DRAWING

The above and other features and advantages of the present invention will become more apparent by describing in detail exemplary embodiments thereof with reference to the attached drawing in which.

DETAILED DESCRIPTION OF THE INVENTION

Figure 1:
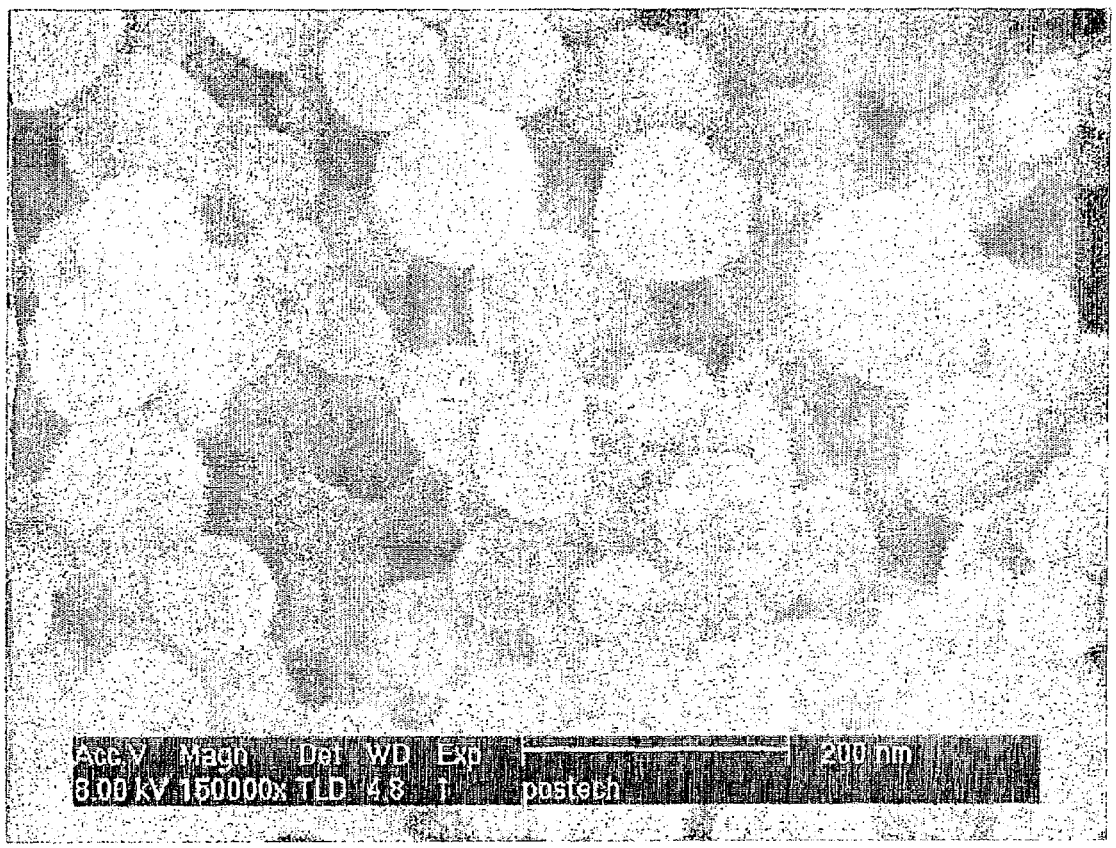
FIG. 1 is a scanning electron microscopic image of nanoparticles prepared using octanesulfanylpropyloxycucurbit[12]uril according to a method of the present invention.

The present invention will be described in detail below.

The present invention provides nanoparticles prepared by the aggregation of cucurbituril derivatives of formula 1 below and having cavities and a particle size of 1 to 1,000 nm:

Formula 1

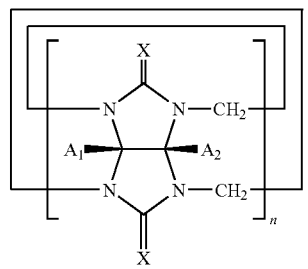

wherein X is O, S, or NH;

$A_1$ and $A_2$ are respectively $OR^1$ and $OR^2$, $SR^1$ and $SR^2$, or $NHR^1$ and $NHR^2$ $R^1$ and $R^2$ are each independently selected from the group consisting of hydrogen, a substituted or unsubstituted alkyl of $C_1$-$C_{30}$, a substituted or unsubstituted alkenyl of $C_2$-$C_{30}$, a substituted or unsubstituted alkynyl of $C_2$-$C_{30}$, a substituted or unsubstituted carbonylalkyl of $C_2$-$C_{30}$, a substituted or unsubstituted thioalkyl of $C_1$-$C_{30}$, a substituted or unsubstituted alkylthiol of $C_1$-$C_{30}$, a substituted or unsubstituted alkoxy of $C_1$-$C_{30}$, a substituted or unsubstituted hydroxyalkyl of $C_1$-$C_{30}$, a substituted or unsubstituted alkylsilyl of $C_1$-$C_{30}$, a substituted or unsubstituted aminoalkyl of $C_1$-$C_{30}$, a substituted or unsubstituted aminoalkylthioalkyl of $C_1$-$C_{30}$, a substituted or unsubstituted cycloalkyl of $C_5$-$C_{30}$, a substituted or unsubstituted heterocycloalkyl of $C_2$-$C_{30}$, a substituted or unsubstituted aryl of $C_6$-$C_{30}$, a substituted or unsubstituted arylalkyl of $C_6$-$C_{20}$, a substituted or unsubstituted heteroaryl of $C_4$-$C_{30}$, and a substituted or unsubstituted heteroarylalkyl of $C_4$-$C_{20}$; and n is an integer of 4 to 20.

The nanoparticles may be formed by the aggregation of a biodegradable polymer in addition to the cucurbituril derivatives. The additional use of the biodegradable polymer reduces the content of the cucurbituril derivative without an adverse effect and minimizes a potential side effect in the human body. Examples of the biodegradable polymer include, but are not limited to, poly(lactide-co-glycolide) (PLGA), polyethyleneglycol (PEG), poly(alkylcyanoacrylate), poly-ε-caprolactone, cellulose derivative, albumin, gelatin, alginate, and a mixture thereof.

Meanwhile, the nanoparticles resulting from the aggregation of the cucurbituril derivatives of formula 1 can be used as a drug carrier. The pharmaceutically active substance is loaded as a guest molecule into the cavities of the nanoparticles.

The pharmaceutically active substance may be an organic compound, a protein, or a gene.

Examples of the organic compound include, but are not limited to, hydrocortisone, prednisolone, spironolactone, testosterone, megesterol acetate, danasole, progesterone, indomethacin, amphotericin B, and a mixture thereof.

Examples of the protein include, but are not limited to, human growth hormone, G-CSF (granulocyte colony-stimulating factor), GM-CSF (granulocyte-macrophage colony-stimulating factor), erythropoietin, vaccine, antibody, insulin, glucagon, calcitonin, ACTH (adrenocorticotropic hormone), somatostatin, somatotropin, somatomedin, parathyroid hormone, thyroid hormone, hypothalamus secretion, prolactin, endorphin, VEGF (vascular endothelial growth factor), enkephalin, vasopressin, nerve growth factor, non-naturally occurring opioid, interferon, asparaginase, alginase, superoxide dismutase, trypsin, chymotrypsin, pepsin, and a mixture thereof.

A method of preparing the nanoparticles include: dissolving the cucurbituril derivative of Formula 1 in an organic solvent to obtain a reaction solution; adding water to the reaction solution followed by dispersing; distilling the dispersed solution in a temperature range from a boiling point of the organic solvent to 100° C. to remove the organic solvent; and cooling the resultant solution to room temperature.

A method of preparing the pharmaceutical composition in which the pharmaceutically active substance as a guest molecule is loaded into the nanoparticles, includes: dissolving the cucurbituril derivative of Formula 1 and the pharmaceutically active substance in an organic solvent to obtain a reaction solution; adding water to the reaction solution followed by dispersing; distilling the dispersed solution in a temperature range from a boiling point of the organic solvent to 100° C. to remove the organic solvent; and cooling the resultant solution to room temperature.

In the methods of preparing the nanoparticles and the pharmaceutical composition, a biodegradable polymer may be dissolved in the organic solvent, together with the cucurbituril derivative, to obtain the reaction solution. The biodegradable polymer may be PLGA, PEG, poly(alkylcyanoacrylate), poly-ε-caprolactone, cellulose derivative, albumin, gelatin, alginate, or a mixture thereof, but is not limited thereto.

The organic solvent is a solvent capable of solubilizing the cucurbituril derivative and may be chloroform, dimethylsulfoxide, dichloromethane, dimethylformamide, tetrahydrofuran, or a mixture thereof, but is not limited thereto.

In adding water to the reaction solution containing the cucurbituril derivative followed by dispersing, water is used in a higher amount than the reaction solution. Preferably, water is used in an amount of more than about 10-fold of the volume of the reaction solution. After the addition of water, the reaction solution must be uniformly dispersed in water. Preferably, the dispersing is carried out by sonication with a sonicator.

After dispersing the reaction solution containing the cucurbituril derivative with water, the organic solvent is removed by distillation with heating above the boiling point of the organic solvent. When the reaction temperature is reduced to room temperature after the removal of the organic solvent, an emulsion is created. Optical microscope, scanning electron microscope, or transmission electron microscope analysis reveals nanoparticles with a particle size of 1 to 1,000 nm.

Hereinafter, the present invention will be described more specifically by Examples. However, the following Examples are provided only for illustrations and thus the present invention is not limited to or by them.

EXAMPLES

Example 1

Preparation of Nanoparticles 1 mg of octanesulfanylpropyloxycucurbit[12]uril was completely dissolved in 0.1 mL of tetrahydrofuran (THF), 10 mL of distilled water was added thereto, and the reaction solution was dispersed by sonication in a sonicator for 10 minutes. Then, the temperature of the sonicator was set to 60° C. to completely remove THF. After the complete removal of THF, the resultant solution was cooled to room temperature to obtain an emulsion. A scanning electron microscopic (SEM) image revealed spherical particles with a particle size of 10 to 200 nm.

The SEM image is shown in FIG. 1.

Example 2

Preparation of Nanoparticles 1 mg of octanesulfanylpropyloxycucurbit[12]uril and 10 mg of PLA were completely dissolved in 0.1 mL of THF, 10 mL of distilled water was added thereto, and the reaction solution was dispersed by sonication in a sonicator for 30 minutes. Then, the temperature of the sonicator was set to 60° C. to completely remove THF. After the complete removal of THF, the resultant solution was cooled to room temperature to obtain an emulsion.

Example 3

Albumin-loaded Nanoparticles 1 mg of octanesulfanylpropyloxycucurbit[12]uril, 5 mg of PLA, and 5 mg of albumin were completely dissolved in 0.1 mL of THF, 10 mL of distilled water was added thereto, and the reaction solution was dispersed by sonication in a sonicator for 30 minutes. Then, the temperature of the sonicator was set to 60° C. to completely remove THF. After the complete removal of THF, the resultant solution was cooled to room temperature to obtain an emulsion. The emulsion was centrifuged at 3,500 rpm and dried.

Example 4

Hydrocortisone-loaded Nanoparticles 1 mg of octanesulfanylpropyloxycucurbit[12]uril, 10 mg of PLA, and 1 mg of hydrocortisone were completely dissolved in 0.1 mL of THF, 10 mL of distilled water was added thereto, and the reaction solution was dispersed by sonication in a sonicator for 30 minutes. Then, the temperature of the sonicator was set to 60° C. to completely remove THF. After the complete removal of THF, the resultant solution was cooled to room temperature to obtain an emulsion. The emulsion was centrifuged at 3,500 rpm and dried.

Example 5

Insulin-loaded Nanoparticles 1 mg of octanesulfanylpropyloxycucurbit[12]uril, 10 mg of PLA, and 1 mg of insulin were completely dissolved in 0.1 mL of THF, 10 mL of distilled water was added thereto, and the reaction solution was dispersed by sonication in a sonicator for 60 minutes. Then, the temperature of the sonicator was set to 60° C. to completely remove THF. After the complete removal of THF, the resultant solution was cooled to room temperature to obtain an emulsion. The emulsion was centrifuged at 4,000 rpm and dried.

Example 6

Calcitonin-loaded Nanoparticles 1 mg of octanesulfanylpropyloxycucurbit[12]uril, 10 mg of PLA, and 2 mg of calcitonin were completely dissolved in 0.1 mL of THF, 10 mL of distilled water was added thereto, and the reaction solution was dispersed by sonication in a sonicator for 30 minutes. Then, the temperature of the sonicator was set to 60° C. to completely remove THF. After the complete removal of THF, the resultant solution was cooled to room temperature to obtain an emulsion. The emulsion was centrifuged at 3,500 rpm and dried.

As described above, the present invention provides nanoparticles formed by the aggregation of cucurbituril derivatives, a pharmaceutical composition in which a drug is loaded into the nanoparticles, and preparation methods thereof.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of preparing a nanoparticle, which comprises
   (a) dissolving a cucurbituril derivative of Formula 1 below in an organic solvent to obtain a reaction solution;
   (b) adding water to the reaction solution followed by dispersing;

(c) distilling the dispersed solution in a temperature range from a boiling point of the organic solvent to 100° C. to remove the organic solvent; and
(d) cooling the resultant solution to room temperature:

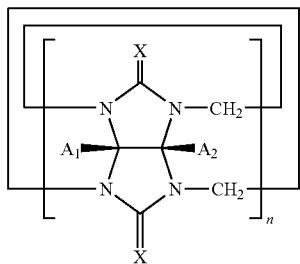

(1)

wherein X is O, S, or NH;

$A_1$ and $A_2$ are respectively $OR^1$ and $OR^2$, $SR^1$ and $SR^2$, or $NHR^1$ and $NHR^2$;

$R^1$ and $R^2$ are each independently selected from the group consisting of hydrogen, a substituted or unsubstituted alkyl of $C_1$-$C_{30}$, a substituted or unsubstituted alkenyl of $C_2$-$C_{30}$, a substituted or unsubstituted alkynyl of $C_2$-$C_{30}$, a substituted or unsubstituted carbonylalkyl of $C_2$-$C_{30}$, a substituted or unsubstituted thioalkyl of $C_1$-$C_{30}$, a substituted or unsubstituted alkylthiol of $C_1$-$C_{30}$, a substituted or unsubstituted alkoxy of $C_1$-$C_{30}$, a substituted or unsubstituted hydroxyalkyl of $C_1$-$C_{30}$, a substituted or unsubstituted alkylsilyl of $C_1$-$C_{30}$, a substituted or unsubstituted aminoalkyl of $C_1$-$C_{30}$, a substituted or unsubstituted aminoalkylthioalkyl of $C_1$-$C_{30}$, a substituted or unsubstituted cycloalkyl of $C_5$-$C_{30}$, a substituted or unsubstituted heterocycloalkyl of $C_2$-$C_{30}$, a substituted or unsubstituted aryl of $C_6$-$C_{30}$, a substituted or unsubstituted arylalkyl of $C_6$-$C_{20}$, a substituted or unsubstituted heteroaryl of $C_4$-$C_{30}$, and a substituted or unsubstituted heteroarylalkyl of $C_4$-$C_{20}$; and n is an integer of 4 to 20:

wherein the nanoparticle is formed by aggregation of the cucurbituril derivatives of Formula 1; and wherein the nanoparticle has a particle size of 10 to 1,000 nm and has a cavity newly formed by the aggregation.

2. The method of claim 1, wherein the cucurbituril derivatives were aggregated with a biodegradable polymer.

3. The method of claim 2, wherein the biodegradable polymer is poly(lactide-co-glycolide) (PLGA), polyethyleneglycol (PEG), poly(alkylcyanoacrylate), poly-ε-caprolactone, cellulose derivative, albumin, gelatin, alginate, or a mixture thereof.

4. The method of claim 1, wherein a biodegradable polymer is further dissolved in the organic solvent together with the cucurbituril derivative in step (a).

5. The method of claim 1, wherein the organic solvent is chloroform, dimethylsulfoxide, dichloromethane, dimethylformamide, tetrahydrofuran, or a mixture thereof.

6. The method of claim 1, wherein the dispersing is carried out by sonication.

7. The method of claim 1, wherein the water is added in an amount of more than about 10-fold of the volume of the reaction solution.

* * * * *